United States Patent
Di Censo et al.

(10) Patent No.: US 9,808,084 B2
(45) Date of Patent: Nov. 7, 2017

(54) TECHNIQUE FOR ADJUSTING THE POSTURE OF A SEATED PERSON

(71) Applicant: HARMAN INTERNATIONAL INDUSTRIES, INC., Stamford, CT (US)

(72) Inventors: Davide Di Censo, San Mateo, CA (US); Stefan Marti, Oakland, CA (US)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 632 days.

(21) Appl. No.: 14/309,710

(22) Filed: Jun. 19, 2014

(65) Prior Publication Data

US 2015/0366350 A1 Dec. 24, 2015

(51) Int. Cl.
  *G06F 19/00* (2011.01)
  *A47C 1/00* (2006.01)
  (Continued)

(52) U.S. Cl.
  CPC .............. *A47C 1/00* (2013.01); *A47C 31/126* (2013.01); *A61B 5/103* (2013.01); *A61B 5/1128* (2013.01); *A61B 5/4561* (2013.01); *A61B 5/6893* (2013.01); *B60N 2/0244* (2013.01); *G05B 13/04* (2013.01); *A61B 3/113* (2013.01); *A61B 2503/22* (2013.01); *A61B 2562/0247* (2013.01); *A61B 2562/046* (2013.01); *B60N 2002/0268* (2013.01)

(58) Field of Classification Search
  CPC ....... A47C 1/00; A47C 31/126; A61B 5/6893; A61B 5/1128; A61B 5/4561; A61B 5/103; A61B 2562/046; A61B 2503/22; A61B 2562/0247; A61B 3/113; B60N 2/0244; B60N 2002/0268; G05B 13/04
  See application file for complete search history.

(56) References Cited

U.S. PATENT DOCUMENTS 5,542,746 A * 8/1996 Bujaryn ................. A47C 13/00
                                                      297/135
6,033,021 A * 3/2000 Udo ....................... A47C 9/002
                                                      297/217.3

(Continued)

FOREIGN PATENT DOCUMENTS

| DE | 102009053312 A1 | 5/2011 |
|----|-----------------|--------|
| WO | 97/42860 A1 | 11/1997 |
| WO | 03/100741 A1 | 12/2003 |
| WO | 2005074754 A1 | 8/2005 |

OTHER PUBLICATIONS

European Search Report dated Nov. 13, 2015 in Application No. 15 16 7612.

*Primary Examiner* — Kidest Bahta
(74) *Attorney, Agent, or Firm* — Artegis Law Group, LLP

(57) ABSTRACT

A posture adjustment system includes a set of sensors coupled to a chair on which a person may sit. The posture adjustment system gathers data from the set of sensors and generates a posture model that reflects a posture associated with the seated person. The posture adjustment system then determines corrections to the posture of the person that could, potentially, improve their posture. The posture adjustment system then indicates those corrections to the person, or, alternatively, applies a set of adjustments to the chair to cause the person to assume a new posture that reflects the posture corrections.

16 Claims, 13 Drawing Sheets

(51) Int. Cl.

| | | |
|---|---|---|
| *A47C 31/12* | (2006.01) | |
| *A61B 5/103* | (2006.01) | |
| *G05B 13/04* | (2006.01) | |
| *A61B 5/00* | (2006.01) | |
| *A61B 5/11* | (2006.01) | |
| *B60N 2/02* | (2006.01) | |
| *A61B 3/113* | (2006.01) | |

(56) References Cited

U.S. PATENT DOCUMENTS

| | | | | |
|---|---|---|---|---|
| 6,078,854 | A * | 6/2000 | Breed | B60N 2/002 |
| | | | | 180/273 |
| 6,422,649 | B2 * | 7/2002 | Hancock | A47C 3/026 |
| | | | | 297/301.5 |
| 8,152,699 | B1 * | 4/2012 | Ma | A61H 1/0229 |
| | | | | 482/54 |
| 2004/0010328 | A1 * | 1/2004 | Carson | G06Q 10/00 |
| | | | | 700/90 |
| 2007/0069564 | A1 * | 3/2007 | Lee | A47C 7/40 |
| | | | | 297/284.4 |
| 2009/0058661 | A1 * | 3/2009 | Gleckler | A61B 5/103 |
| | | | | 340/573.7 |
| 2012/0119552 | A1 * | 5/2012 | Kao | A47C 7/006 |
| | | | | 297/325 |
| 2013/0117158 | A1 * | 5/2013 | Cvek | G06Q 30/0623 |
| | | | | 705/26.63 |

* cited by examiner

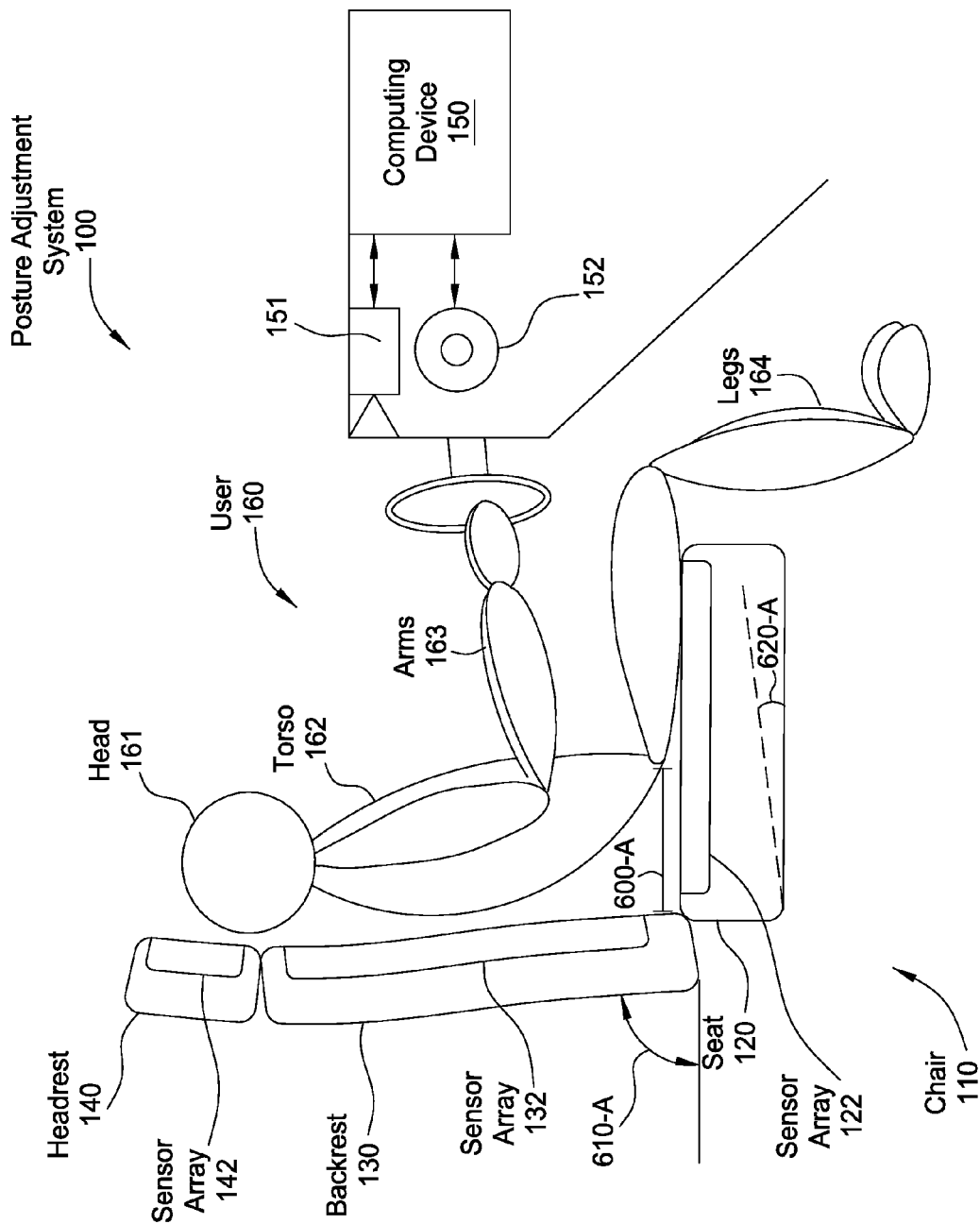

TECHNIQUE FOR ADJUSTING THE POSTURE OF A SEATED PERSON

BACKGROUND

Field of the Embodiments of the Invention

Embodiments of the present invention relate generally to adjustable chairs, and, more specifically, to a technique for adjusting the posture of a seated person.

Description of the Related Art

A person may sit down in a wide variety of different contexts, including driving an automobile, working at a desk, relaxing in a chair, and so forth. When seated, people may assume a range of bodily positions. Such bodily positions are generally known as postures. Typically, a given person habitually assumes a specific set of postures when seated. Some habitual postures may be benign; however, certain other habitual postures may cause physical problems over time. For example, when a person habitually sits with a slouched posture, that person could experience chronic spinal problems.

Some types of chairs are configurable and can be manually adjusted to support specific healthy postures and preclude detrimental postures. In particular, chairs within modern automobiles oftentimes include different sections that can be independently adjusted via motorized controls. A modern driver's seat, for example, could include a motorized backrest that can be adjusted via a control panel. A user of a configurable chair may position the sections of the chair to facilitate specific healthy postures.

However, one drawback associated with conventional adjustable chairs is that a given person may not be aware of the posture(s) with which they sit, and may thus be ill informed to adjust such a chair properly. When the person habitually assumes a health-adverse posture, such as a slouched posture, that person may inadvertently adjust the chair in such a way that facilitates slouching. Further, in situations where the chair is, in fact, adjusted properly, a person seated in that chair may unconsciously assume a health-adverse posture despite the correct adjustment of the chair.

As the foregoing illustrates, people may inadvertently assume health-adverse postures when sitting down. When a person sits in a conventional adjustable chair, the person may also incorrectly adjust the chair to facilitate health-adverse postures, potentially causing chronic health problems over time.

SUMMARY

One or more embodiments set forth include a non-transitory computer-readable medium storing program instructions that, when executed by a processing unit, cause the processing unit to effect modifications to the posture of a seated person, by performing the steps of acquiring sensor data that reflects a current posture associated with the seated person, determining at least one modification to make to the current posture to change the current posture to a modified posture, and causing one or more changes in a position or orientation of a chair in which the seated person is sitting to be automatically effected, based on the at least one modification, to change the current posture to the modified posture, or causing the one or more changes to be communicated to the seated person.

At least one advantage of the present invention is that the health and well being of a user of the posture adjustment system may be improved. When a user habitually sits with a posture that may be detrimental to their health, the posture adjustment system is capable of identifying the detrimental posture and taking corrective action.

BRIEF DESCRIPTION OF THE SEVERAL VIEWS OF THE DRAWINGS

So that the manner in which the recited features of the one more embodiments set forth above can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the invention subsumes other embodiments as well.

FIGS. 3A-6B illustrate exemplary scenarios in which the posture adjustment system of FIG. 1 is used to improve the posture of a seated person, according to various embodiments;

DETAILED DESCRIPTION

In the following description, numerous specific details are set forth to provide a more thorough understanding of certain specific embodiments. However, it will be apparent to one of skill in the art that other embodiments may be practiced without one or more of these specific details or with additional specific details.

Figure 1:
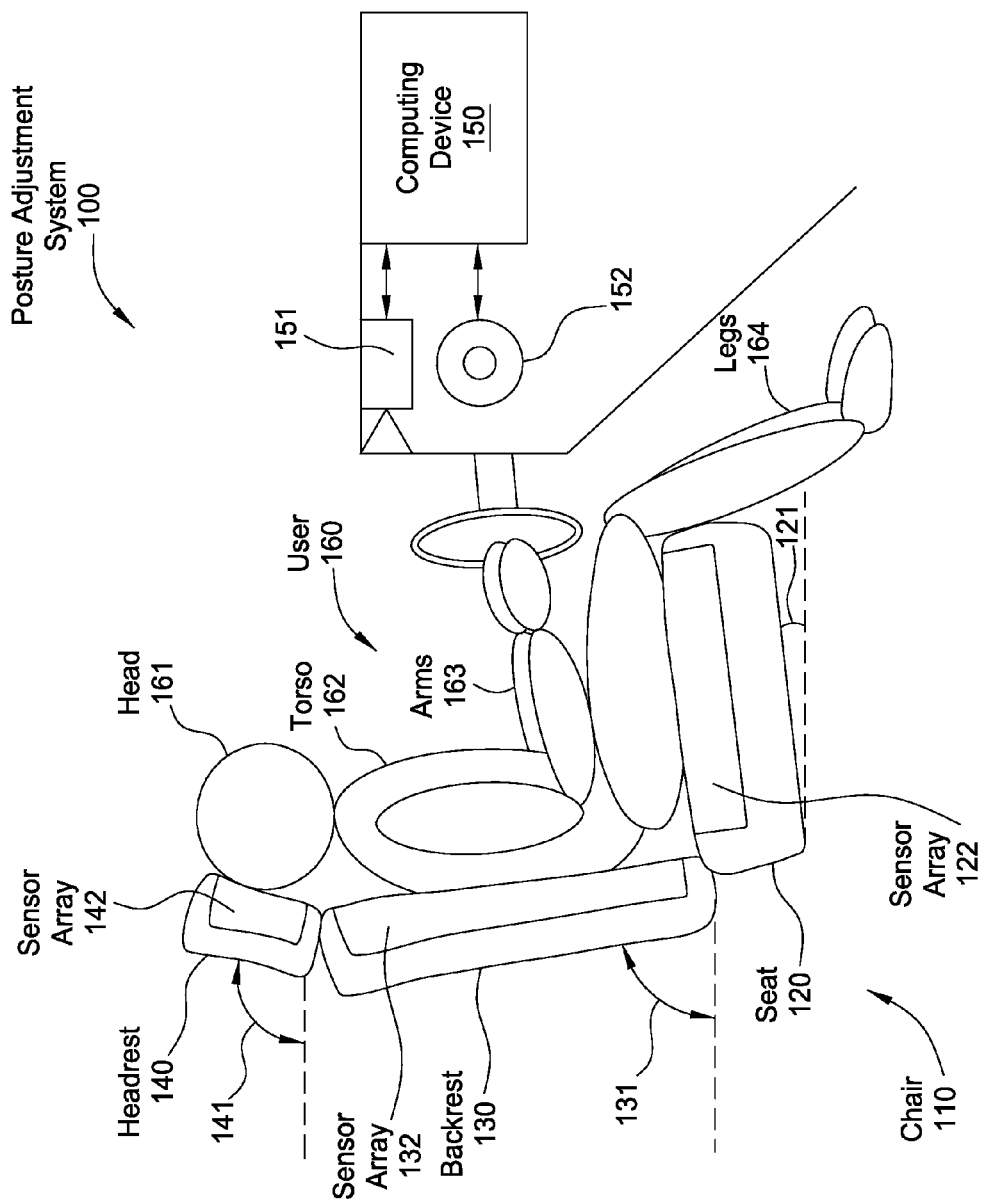
FIG. 1 illustrates a posture adjustment system configured to adjust the posture of a seated person, according to various embodiments.

FIG. 1 illustrates a posture adjustment system configured to adjust the posture of a seated person, according to various embodiments. As shown, posture adjustment system 100 includes a chair 110 that, in turn, includes a seat 120, a backrest 130, and a headrest 140. Posture adjustment system 100 also includes a computing device 150 configured to manage the overall operation of the various components of posture adjustment system 100.

As also shown, a user 160 is seated on chair 110. Posture adjustment system 100 is configured to monitor the posture of user 160 and to then identify certain posture corrections or modifications that may be beneficial to user 160. Posture adjustment system 100 may then notify user 160 of those corrections, and/or adjust chair 110 to effect those corrections. Thus, posture adjustment system 100 is configured to improve the posture of user 160. In the context of this disclosure, the "posture" of user 160 includes the position and/or orientation of one or more body parts associated with user 160. Those body parts include, without limitation, head 161, torso 162, arms 163, and legs 164, among others not specifically labeled in FIG. 1 without limitation.

The posture of user 160 may depend on the configuration of chair 110. That configuration is determined by various angles and/or positions associated with seat 120, backrest 130, and headrest 140. As is shown, seat 120 is positioned at an angle 121, backrest 130 is positioned at an angle 131, and headrest 140 is positioned at an angle 141. Each of the aforementioned chair sections is independently adjustable via one or more motors (none shown here). For example, and without limitation, a motor coupled to seat 120 could adjust angle 121 of seat 120, a motor coupled to backrest 130 could adjust angle 131, and a motor coupled to headrest 140 could adjust angle 141. Computing device 150 is configured to control the position and/or angle of a given section of chair 110 by issuing motor control signals to the one or more motors coupled to that chair section.

The sections of chair 110 also include various sensor arrays. Seat 120 includes sensor array 122, backrest 130 includes sensor array 132, and headrest 140 includes sensor array 142. Sensor arrays 122, 132, and 142 within seat 120, backrest 130, and headrest 140, respectively, gather data that may indicate the current posture of user 160. Specifically, each different sensor array may gather data that reflects the position, orientation, and/or pressure distribution of one or more body parts of user 160.

For example, and without limitation, sensor array 122 within seat 120 gathers data that could indicate the weight distribution of user 160 on seat 120. Likewise, sensor array 132 within backrest 130 gathers data that could indicate a set of positions along backrest 130 where torso 162 of user 160 exerts different pressures. Similarly, sensor array 142 within headrest 140 gathers data that could indicate an angle associated with head 161 of user 160. Persons skilled in the art will recognize that the aforementioned examples are provided for illustrative purposes only, and are not meant to limit the scope of the present invention. As a general matter, any sensor array within posture adjustment system 100 may be configured to measure any physical property associated with user 160.

Sensor arrays 122, 132, and 142 may include a wide variety of different types of sensors configured to measure physical properties associated with user 160. For example, sensor arrays 122, 132, and 142, respectively, could include pressure sensors, touch sensors, thermal sensors, and so forth, without limitation. Computing device 150 may be coupled to seat 120, backrest 130, and headrest 140 and configured to acquire sensor data generated by sensor arrays 122, 132, and 142. Computing device 150 may also be configured to acquire sensor data gathered by an optical sensor 151.

Optical sensor 151 is configured to record optical data associated with user 160. Optical sensor 151 could be a video camera, an infrared (IR) sensor, a red-green-blue (RGB) imager, a depth indicator, a time-of-flight sensor, a laser-based instrument, or another type of device that is sensitive to optical signals, without limitation. Based on the sensor data provided by optical sensor 151, as well as that provided by sensor arrays 122, 132, and 142, computing device 150 generates a posture model that represents the current posture of user 160. The posture model could include, for example, a set of positions and/or angles associated with head 161, torso 162, arms 163, and legs 164 of user 160, among other possible types of multi-dimensional models, without limitation.

When generating the posture model, computing device 150 may implement a wide variety of different computing techniques to process any of the aforementioned sensor data. For example, and without limitation, computing device 150 could implement computer vision techniques to process optical sensor data generated by optical sensor 151, and then generate a multi-dimensional model based on the processed sensor data (and, potentially, sensor data from sensor arrays 122, 132, and 142). In doing so, computing device 150 could execute computer vision algorithms locally, or rely on a cloud-based service that implements computer vision techniques remotely to generate the posture model, without limitation. Computing device 150 may also offload any processing operations onto locally accessible devices, including, e.g., a smartphone, tablet computer, smart watch or any other wearable, etc., without limitation.

Computing device 150 may generate a wide variety of different types of posture models based on the acquired sensor data. For example, and without limitation, computing device 150 could generate a three-dimensional model of each body part associated with user 160, including head 162, torso 162, arms 163, and legs 164, among others, along with a set of physical equations that represent the dynamics of those body parts and/or constraints associated with the body parts. Computing device 150 may also model linkages between body parts of user 160, such as, e.g., the neck or the hip joint of user 160, without limitation. Any technically feasible approach to multidimensional modeling falls within the scope of the various embodiments of the present invention.

Persons familiar with multidimensional models of the human body will readily recognize that the body parts shown in FIG. 1 are provided for exemplary purposes only, and that computing device 150 may generate a posture model having any technically feasible granularity or level of detail beyond what is shown. For example, and without limitation, computing device 150 could model the face of user 160, the fingers of user 160, and potentially other finer details of user 160, such as eye-gaze direction, without limitation.

Upon generating the posture model in the fashion described above, computing device 150 then compares the posture model to an ergonomic model. The ergonomic model reflects an optimal posture for user 160. In the context of this disclosure, an "optimal" posture generally refers to a posture that is unlikely to cause chronic physical problems for user 160 over time, or simply one that is likely to be comfortable for user 160. The ergonomic model may be based on statistical medical data that indicates postures that, historically, have not caused chronic physical problems for people. As a general matter, the ergonomic model reflects a posture that is conducive to the physical well being of user 160.

Computing device 150 compares the posture model of user 160 to the ergonomic model to determine posture corrections that could, potentially, cause user 160 to assume a posture that reflects the ergonomic model. Computing device 150 may also rely on other data when determining the aforementioned posture corrections. For example, and without limitation, computing device 150 could rely on a set of user preferences provided by user 160 that indicate a posture user 160 wishes to assume. Computing device 150 could also rely on posture recommendations provided by a health professional, such as an orthopedist, a chiropractor, a physical fitness instructor, and so forth, without limitation.

Either of the user preferences or the posture recommendations mentioned above may also constitute a model of the posture of user 160 to which the posture model may be compared, in various embodiments of the present invention. For example, and without limitation, computing device 150 could generate a "preferred" posture model that is based on the preferences of user 160. Further, computing device 150 could generate a "recommended" posture model that is based on the posture recommendations received from the health professional, without limitation. In computing the posture corrections, computing device 150 could compare the posture model to any one or more of the posture model, the preferred posture model, and the recommended posture model. Computing device 150 could also merge the ergonomic model with the preferred posture model and the recommended posture model to generate a target posture model, and then determine the posture corrections by comparing the posture model to the target posture model. Those skilled in the art will understand that a wide variety of techniques exist for computing posture corrections, and that those discussed above are provided for exemplary purposes only, without limitation.

Once computing device 150 has determined posture corrections for user 160, computing device 150 may notify user 160 of those posture corrections. Computing device 150 may audibly communicate the posture corrections to user 160 via speaker 152, or visually notify user 160 of those corrections (e.g., via a display device that is not shown). For example, computing device 150 could output voice commands via speaker 152 that instruct user 160 to lean back, sit upright, etc., without limitation. Computing device 150 could also display visual data that indicates such posture corrections, including, e.g., a visual simulation of user 160 assuming a posture that incorporates the posture corrections, without limitation. With this approach, posture adjustment system 100 may increase the self-awareness of user 160 by providing valuable insight into their current posture, as well as information regarding potentially better postures that user 160 may assume.

Computing device 150 may also determine specific adjustments to chair 110 that, when implemented, cause user 160 to assume a posture that incorporates the posture corrections. In doing so, computing device 150 may rely on chair-posture mapping data that indicates relationships between changes in the position of each chair section and corresponding changes in the posture of user 160. For example, the chair-posture mapping could indicate that increasing angle 141 of headrest 140 would cause head 161 of user 160 to tilt forward, among other analogous mappings. Based on the posture corrections, and based on the chair-posture mapping data, computing device 150 then determines chair adjustments that would effect the posture corrections. For example, and without limitation, if user 160 slouches in chair 110, computing device 150 could determine a specific increase to angle 121 of seat 120 that would preclude such slouching. Computing device 150 is configured to implement the chair adjustments by issuing motor control signals to motors associated with seat 120, backrest 130, and/or headrest 140.

Computing device 150 may notify user 160 of recommended posture corrections, or effect those posture corrections via adjustments of chair 110, simultaneously or at different times. Computing device 150 may also optionally issue notifications or perform adjustments to chair 110 depending on various environmental factors. For example, and without limitation, when chair 110 resides within an automobile, computing device 150 could perform adjustments to chair 110 only when that automobile is stationary, and issue notifications otherwise. Computing device 150 may also selectively issue notifications or perform adjustments to chair 110 depending on the determined posture correction(s). For example, and without limitation, computing device 150 could determine that a certain posture correction cannot be implemented via adjustments to chair 110, and could then issue a notification to effect that correction.

Additionally, computing device 150 may notify user 160 of posture modifications that will be made via adjustments to chair 110 in advance of actually performing those adjustments. For example, and without limitation, computing device 150 could determine that backrest 130 should be reclined slightly in order to effect a particular posture modification, and then indicate to user 160 that such an adjustment will occur before actually performing the adjustment. Further, computing device 150 may be responsive to user input for a short period of time after providing the notification, allowing user 160 to "opt out" of the imminent chair adjustment. Such functionality may reduce the likelihood that chair adjustments will startle user 160 and increase the user control over when such adjustments can be made, thereby improving the safety of posture adjustment system 100.

Although the foregoing discussion provides various examples of scenarios where computing device 150 within posture adjustment system 100 issues notifications and/or performs adjustments to chair 110, those examples are not meant to be limiting. As a general matter, any technically feasible manner of determining when to issue notifications and/or perform adjustments to chair 110 falls within the scope of the present invention.

With the techniques described herein, posture adjustment system 100 is capable of monitoring the posture of user 160 and then determining specific posture corrections for user 160. Those posture corrections may improve the health of user 160 or mitigate pre-existing physical ailments. Persons skilled in the art will recognize that the various approaches described thus far are applicable to any sort of adjustable chair. Although FIG. 1 illustrates chair 110 within an automobile, the aforementioned techniques are equally applicable to office chairs, airplane seats, movie theater chairs, home entertainment chairs (e.g., a La-Z-Boy® chair, without limitation), gaming chairs, and any other type of configurable furniture on which a person may sit.

In one embodiment, a chair configured to implement the techniques described herein may perform adjustments based on an audio source. For example, and without limitation, a home entertainment chair could effect posture changes based on a surround sound audio source, and further, could perform specific posture adjustments based on directionality associated with that surround sound audio source. In another embodiment, a chair configured to implement the aforementioned techniques may be coupled to a gaming system and configured to effect posture adjustments based on a state of gameplay associated with a game.

In addition, the techniques described herein may be extended to include chairs with a variety of different adjustable chair sections. For example, and without limitation, posture adjustment system 100 could include an armrest coupled to chair 110 that includes a sensor array. Posture adjustment system 100 could alter the position of arms 163 of user 160 by adjusting the position of that armrest. Generally, chair 110 may include any manner of different adjustable sections with integrated sensor arrays. All such configurations fall within the scope of the present invention.

Posture adjustment system 100 may also include sensor arrays integrated into various other places, aside from chair 110. For example, in the context of an automobile, a steering wheel within that automobile could include touch sensors that monitor the position of the hands of user 160. Posture adjustment system 100 could instruct user 160 to maintain proper hand positioning, or adjust the position of that steering wheel to improve the posture of user 160. Posture adjustment system 100 could also include thermal pads coupled to the steering wheel that guide the hands of user 160 to correct hand positions, e.g., by increasing the temperature of the steering wheel at correct hand positions, and decreasing the temperature at other, incorrect positions, without limitation.

In various embodiments, posture adjustment system 100 may perform adjustments beyond those intended to directly influence the posture of user 160. For example, and without limitation, once posture adjustment system 100 has caused user 160 to assume a new posture, posture adjustment system 100 could then reposition a set of mirrors within an automobile driven by user 160. Posture adjustment system 100 could reposition the set of mirrors relative to the new posture of user 160 in order to increase visibility for user 160. As a general matter, posture adjustment system 100 may perform any type of adjustment to any object in the vicinity of user 160 in response to user 160 assuming a new posture.

Posture adjustment system 100 may also be configured to identify particular use-cases, and effect different posture corrections based on the identified use-case. For example, and without limitation, when posture adjustment system 100 is integrated into an automobile, computing device 150 could identify that user 160 has embarked on a long commute, and, in response, effect posture corrections that reflect a relaxed and comfortable posture. Alternatively, computing device 150 could identify that user 160 is engaged in complex city driving, and, in response, effect posture corrections that facilitate increased alertness and visibility. In any scenario, persons skilled in the art will recognize that embodiments of the posture adjustment system 100 may be configured to perform any adjustments to the posture of user 160 slowly enough or over a long enough duration of time to avoid startling, surprising or otherwise distracting the user 160. Further, in various embodiments, a user-interface alert may be implemented to inform the user 160 that adjustments to the posture of user 160 are about to begin. Such an alert may precede any such adjustments and may be implemented in a variety of different ways, such as a voice cue or a light on the vehicle dash or instrument cluster, to announce or notify the user 160 of the upcoming changes.

In various other embodiments, posture adjustment system 100 may perform posture corrections, via notifications or adjustments to chair 110, based on trends associated with user 160. For example, and without limitation, computing device 150 within posture adjustment system 100 could analyze sensor data recorded over time to identify that user 160 frequently leans forward after sitting in chair 110 for 30 minutes. Computing device 150 could then anticipate this behavior of user 160, and, 30 minutes after user 160 sits down, automatically issue a notification that instructs user 160 to lean back.

In performing the aforementioned functionality, computing device 150 could record sensor data over a long time period, and then identify characteristic patterns within that sensor data that correlate to specific times (as mentioned in the example above) or correlate to specific other identifiable events. For example, computing device 150 could identify that user 160 prefers a "relaxed" posture when cruise control is activated. Then, whenever user 160 activates cruise control, computing device 150 could effect posture modifications that facilitate a more relaxed posture. As a general matter, computing device 150 may process any amount of sensor data to identify patterns associated with user 160, and then effect posture modifications for user 160 based on those patterns. The posture modifications could be intended to improve the posture of user 160, or simply intended to increase the comfort of user 160, without limitation. Again, as previously set forth herein, embodiments of the posture adjustment system 100 may be configured to perform any adjustments to the posture of user 160 slowly enough or over a long enough duration of time to avoid startling, surprising or otherwise distracting the user 160. Further, in various embodiments, a user-interface alert may be implemented to inform the user 160 that adjustments to the posture of user 160 are about to begin. Such an alert may precede any such adjustments and may be implemented in a variety of different ways, such as a voice cue or a light on the vehicle dash or instrument cluster, to announce or notify the user 160 of the upcoming changes.

In one embodiment, when observing trends in the posture of user 160 over a period of time, computing device 150 may generate a time-varying posture model that reflects changes in the posture of user 160 over time. That time-varying posture model may also reflect environmental data, such as sensor readings associated with an automobile driven by user 160, which potentially correlate with the posture of user 160 at a given time. By analyzing the time-varying posture model and corresponding environmental data, computing device 150 may anticipate the behavior of user 160 and then effect posture changes for user 160 earlier than otherwise possible.

Posture adjustment system 100 may also be configured to identify different users (such as user 160 or other users) and to implement different posture corrections based on the identified user. Computing device 150 within posture adjustment system 100 could, for example, and without limitation, maintain separate user profiles, each of which includes a specific ergonomic model, set of user preferences, and set of posture recommendations. Computing device 150 could identify the different users based on biometric data gathered by sensor arrays 122, 132, and 142, visual data gathered by optical sensor 151, voice recognition, or recognition of a discrete identification device worn by each user, such as a wristband.

In the foregoing explanation, the functionality of posture adjustment system 100 has been described relative to the exemplary illustration show in FIG. 1. However, those of ordinary skill in the art will understand that FIG. 1 is provided solely as an example, and not meant to limit the scope of the present invention. In particular, as stated above, posture adjustment system 100 need not be specifically integrated into an automobile. Further, posture adjustment system 100 may be incorporated into any type of furniture, beyond chairs.

For example, and without limitation, posture adjustment system 100 could be configured to effect posture changes for a user within the context of an office setting. In such an environment, posture adjustment system 100 could include sensor arrays integrated into an office chair on which the user sits, and/or optical sensors position on a desk where the user works, without limitation. The office chair could include motorized sections, similar to chair 110 shown in FIG. 1, which could be adjusted to effect posture modifications for the user. Posture adjustment system 100 could also notify the user of suggested posture changes, in similar fashion as discussed above. In the office environment discussed in this example, the user could perform work-related tasks at a computer workstation, where that workstation could also be configured to implement any of the functionality of computing device 150 shown in FIG. 1, without limitation.

In another example, and without limitation, posture adjustment system 100 could be integrated into an airplane seat and configured to modify the posture of an airplane passenger. The airplane seat could include sensor arrays and/or optical sensors configured to gather data that reflects the posture of the passenger. A computing device within the airplane would process the sensor data, generate a posture model, and then determine posture corrections that could, potentially, improve the posture of the passenger. Those posture corrections could be conveyed to the user via headphones that the user wears, a display device within a seatback, and so forth, without limitation. The posture corrections could also be effected via automatic seat adjustments, in keeping with the features of posture adjustment system 100 described thus far. A single computing device could be associated with multiple seats and configured to determine posture corrections for those multiple seats, or a different computing device could be associated with each airplane seat and configured to determine posture corrections for just one seat, among other possibilities, and without limitation.

In one embodiment, posture adjustment system 100 aggregates posture data across multiple users seated in a group of chairs and then determines posture adjustments for those users based on the aggregated data. For example, and without limitation, posture adjustment system 100 could identify that a subset of the multiple users are slouching, and then adjust the group of chairs as a whole to preclude slouching across all of the multiple users, thereby proactively preventing slouching for those users.

In addition, when implemented in the context of air travel, posture adjustment system 100 could identify likely use-cases for the airplane passenger and determine posture corrections that reflect an identified use case. For example, and without limitation, posture correction system 100 could identify that the passenger is eating, and determine posture corrections that facilitate eating. Posture adjustment system 100 could perform such an identification based on a variety of data, including the position of a tray table associated with the passenger, the current time, notifications provided by the airplane staff, and so forth. Posture adjustment system 100 may also provide other health-related information to the passenger, beyond posture-relative notifications. For example, posture adjustment system 100 could monitor the amount of time that the passenger has been seated, and then recommend that the passenger take a brief walk, stretch, etc., in order to avoid stiffness, blood clots, and so forth, without limitation. Persons skilled in the art will recognize that the aforementioned functionality is broadly applicable to posture adjustment systems that operate in a wide variety of different contexts, beyond air travel, and without limitation.

As a general matter, any system configured to monitor the position of one or more body parts of a human being, and then effect an adjustment to that body part, falls within the scope of the present invention. In addition, any system configured to effect such an adjustment relative to an optimal posture, a preferred posture, a recommended posture, or another type of target posture or combination thereof, also falls within the scope of the present invention. Furthermore, any system configured to effect a posture adjustment in response to an environmental cue, an identifiable event, a recurring pattern, or a characteristic sequence of events, also falls within the scope of the posture adjustment system 100 described herein.

Figure 2:
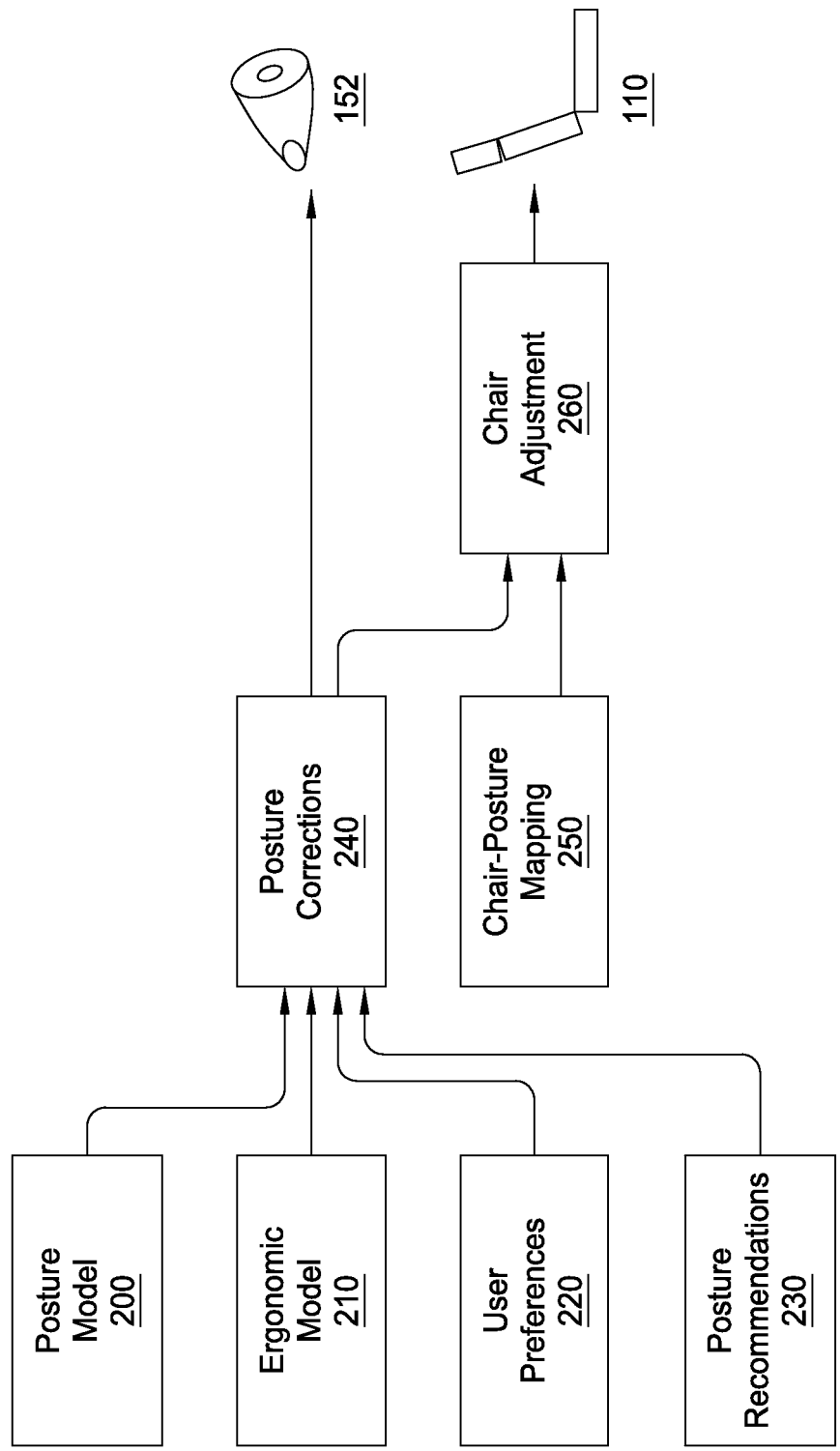
FIG. 2 illustrates data that is processed by the posture adjustment system of FIG. 1 when adjusting the posture of a seated person, according to various embodiments.

FIG. 2 illustrates a data flow associated with managing the overall functionality of posture adjustment system 100 when modifying the posture of user 160, according to various embodiments. As shown, posture model 200, ergonomic model 210, user preferences 220, and posture recommendations 230 represent data associated with that data flow. Posture model 200, ergonomic model 210, user preferences 220, and posture recommendations 230 may be acquired, processed, and/or generated by computing device 150 shown in FIG. 1. Computing device 150 generates posture model 200 based on sensor data gathered by sensor arrays 122, 132, and 142, as well as optical data gathered by optical sensor 151. Computing device 150 may implement any technical feasible approach to modeling when generating posture model 200, including computer-vision techniques, free-body modeling, and so forth, without limitation.

Computing device 150 may acquire ergonomic model 210 from an external source, such as an online database, or may be programmed to include ergonomic model 210, without limitation. Ergonomic model 210 reflects an "optimal" posture that user 160 may wish to assume. The optimal posture may be a comfortable posture, or may represent a specific posture that is unlikely to cause health problems for user 160. User preferences 220 indicate a set of preferences that user 160 has configured, e.g., via interaction with computing device 150, without limitation. User preferences 220 could indicate a particular seat angle or a specific position for a body part of user 160, among other examples, and without limitation. Posture recommendations 230 may be acquired from a medical professional and generally indicate postures that the medical professional believes will benefit user 160.

Computing device 150 compares posture model 200 to ergonomic model 210, user preferences 220, and posture recommendations 230 and identifies posture corrections 240 that may, potentially, be applied to the posture of user 160 in order to improve that posture. Specifically, posture corrections 240 may indicate changes to the posture of user 160 that would reduce differences between posture model 200 and ergonomic model 210, user preferences 220, and posture recommendations 230. In various embodiments, computing device 150 generates posture corrections 240 based on any one of posture model 200, ergonomic model 210, user preferences 220, and posture recommendations 230, or any combination thereof.

Computing device 150 may then notify user 160 of posture corrections 240 by communicating those posture corrections to user 160. Computing device 150 could audibly output posture corrections 240 to user via speaker 152, visually display those corrections to user 160, and so forth, without limitation. User 160 may then assume a new posture that incorporates posture corrections 240. Computing device 150 may also generate chair adjustments 260 that can be applied to chair 110 in order to cause user 160 to assume a posture that reflects posture corrections 240. In doing so, computing device 150 relies on chair-posture mapping 250, which indicates relationships between changes in the position of each chair section and corresponding changes in the posture of user 160. Computing device 150 applies chair adjustments 260 to chair 110 in order to cause user 160 to assume a new posture that incorporates posture corrections 240.

Persons skilled in the art will understand that the data flow diagram shown in FIG. 2 is provided for illustrative purposes only, and not meant to limit the scope of the invention. Further, persons skilled in the art will recognize that posture adjustment system 100 may rely on computing device to implement any portion of processing described here, and that computing device 150 need not exhaustively perform all branches shown in FIG. 2. For example, and without limitation, computing device 150 could generate posture corrections 240 based solely on posture model 200 and user preferences 220, and then simply output those corrections to user 160 without generating or applying chair adjustments 260.

Figure 3A:
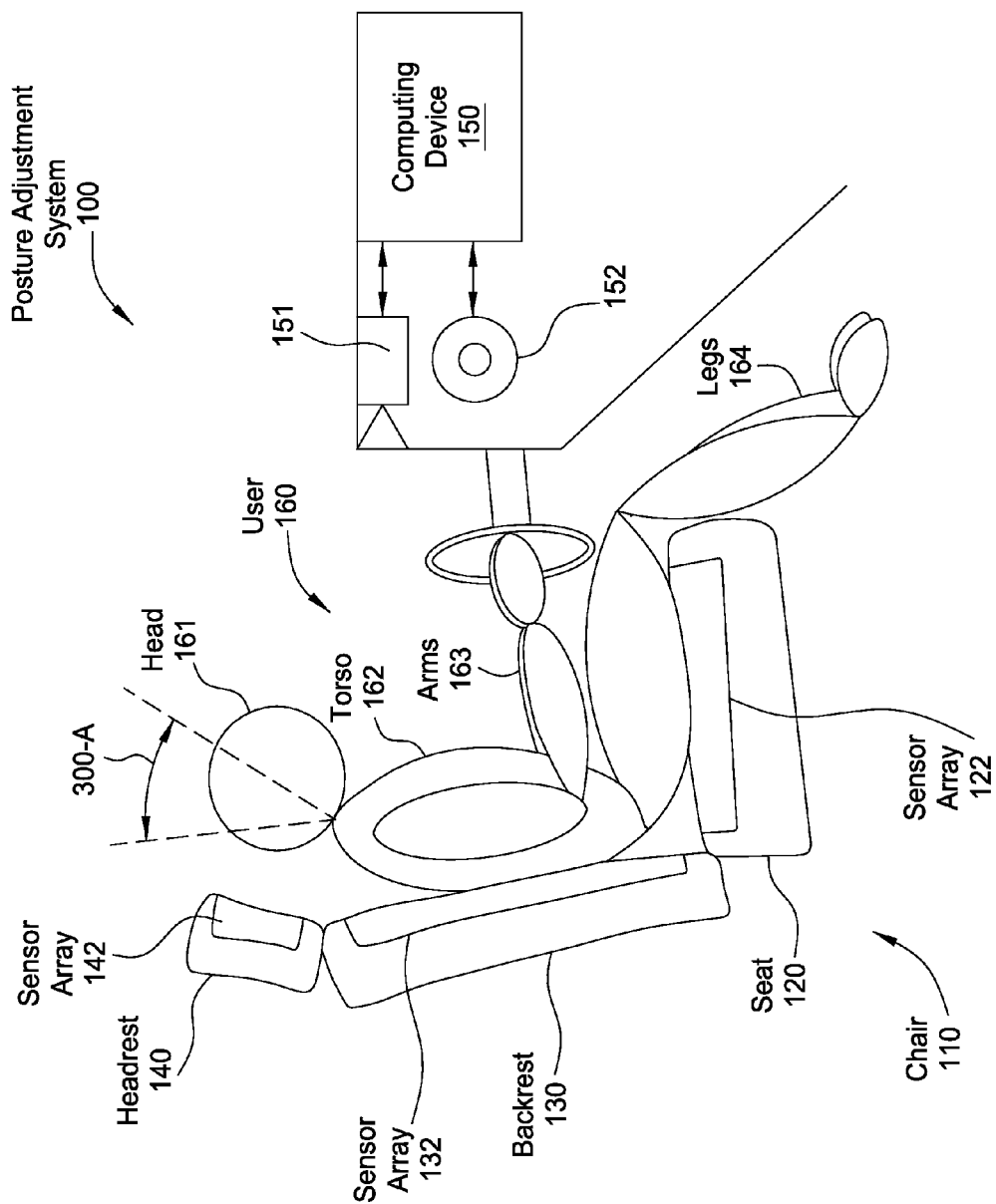
Figure 3B:
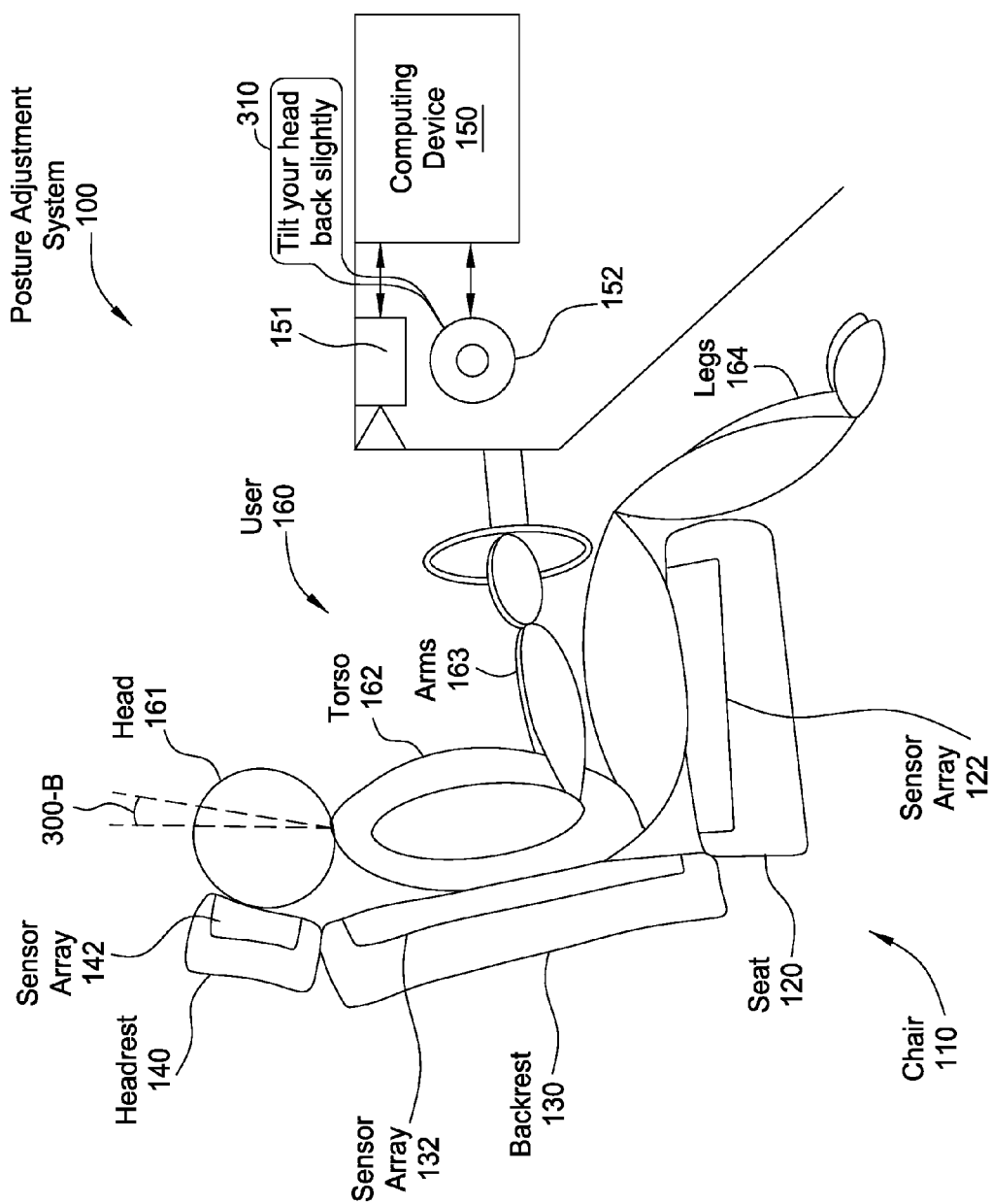

FIGS. 3A-3B illustrate an exemplary scenario where posture adjustment system 100 of FIG. 1 suggests a posture correction to user 160 to modify a head angle that may be uncomfortable or health-adverse, according to various embodiments. As shown in FIG. 3A, head 161 of user 160 is tilted forward by an angle 300-A. With this posture, user 160 could potentially experience neck pain over time.

Computing device 150 is configured to acquire sensor data gathered by sensor arrays 122, 132, 142, and/or optical sensor 151, and to generate a posture model (such as posture model 200 shown in FIG. 2). The posture model reflects the current posture of user 160, including angle 300-A of head 161. Computing device 150 identifies a posture correction that represents a decrease of angle 300-A, and then notifies user 160 of this posture correction, as described in greater detail below in conjunction with FIG. 3B.

As shown in FIG. 3B, computing device 150 issues a notification 310 to user 160 that instructs user 160 to tilt their head back slightly. In response, user 160 may tilt head 161 back to a reduced angle 300-B. With this new posture, user 160 may avoid potential neck pain.

Figure 4A:
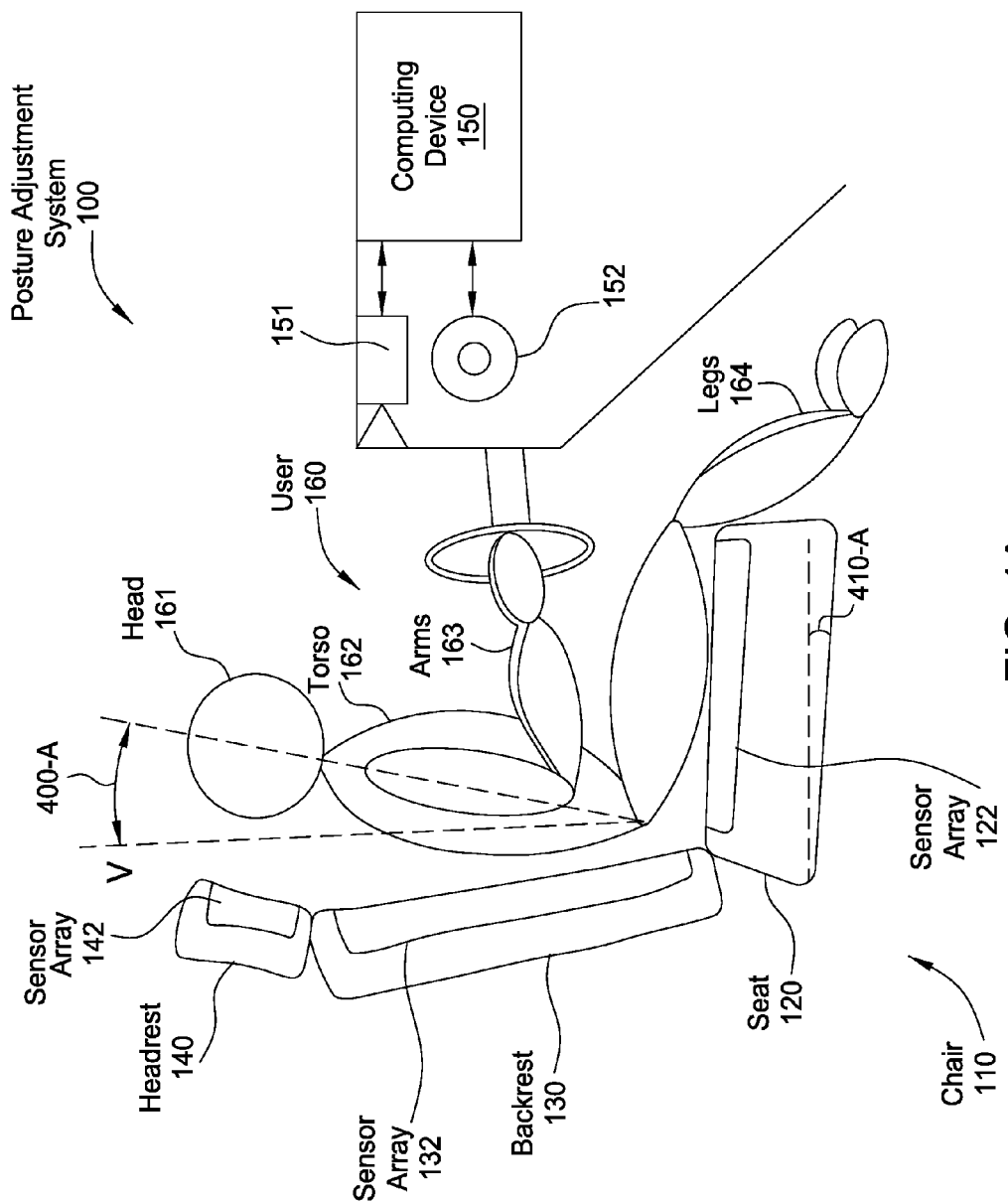
Figure 4B:
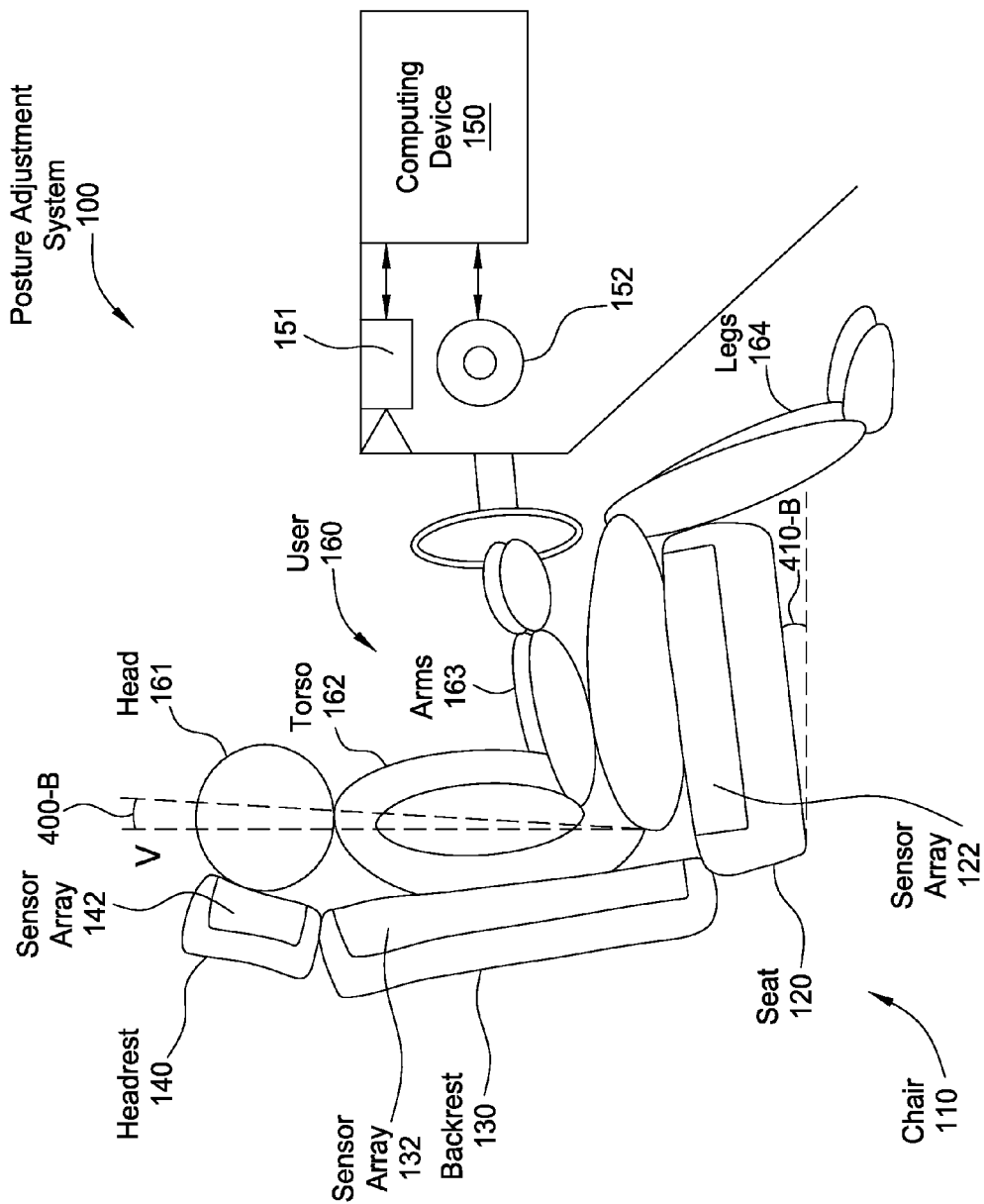

FIGS. 4A-4B illustrate an exemplary scenario where posture adjustment system 100 of FIG. 1 effects a posture correction for user 160 to modify a back angle that may be uncomfortable or health-adverse, according to various embodiments. As shown in FIG. 4A, torso 162 of user 160 is tilted forward by an angle 400-A. With this posture, user 160 could potentially experience back pain over time.

Computing device 150 is configured to acquire sensor data and then generate a posture model that reflects the current posture of user 160. The posture model could, in this example, include angle 400-A of torso 161, without limitation. Computing device 150 identifies a posture correction that represents a decrease of angle 400-A, and then determines specific adjustments to chair 110 that may cause user 160 to assume a new posture that incorporates the posture correction. In doing so, computing device 150 identifies a relationship between angle 400-A associated with user 160 and angle 410-A of seat 120. Chair-posture mapping 250 shown in FIG. 2 could indicate that relationship, among other possibilities, without limitation. Computing device 150 then applies the determined adjustments to chair 110 to effect the posture corrections, as described in greater detail below in conjunction with FIG. 4B.

As shown in FIG. 4B, computing device 150 has increased 410-A to angle 410-B, thereby elevating seat 120 slightly. In response, user 160 has leaned back from angle 400-A to angle 400-B. With this new posture, user 160 may avoid potential back pain.

Figure 5A:
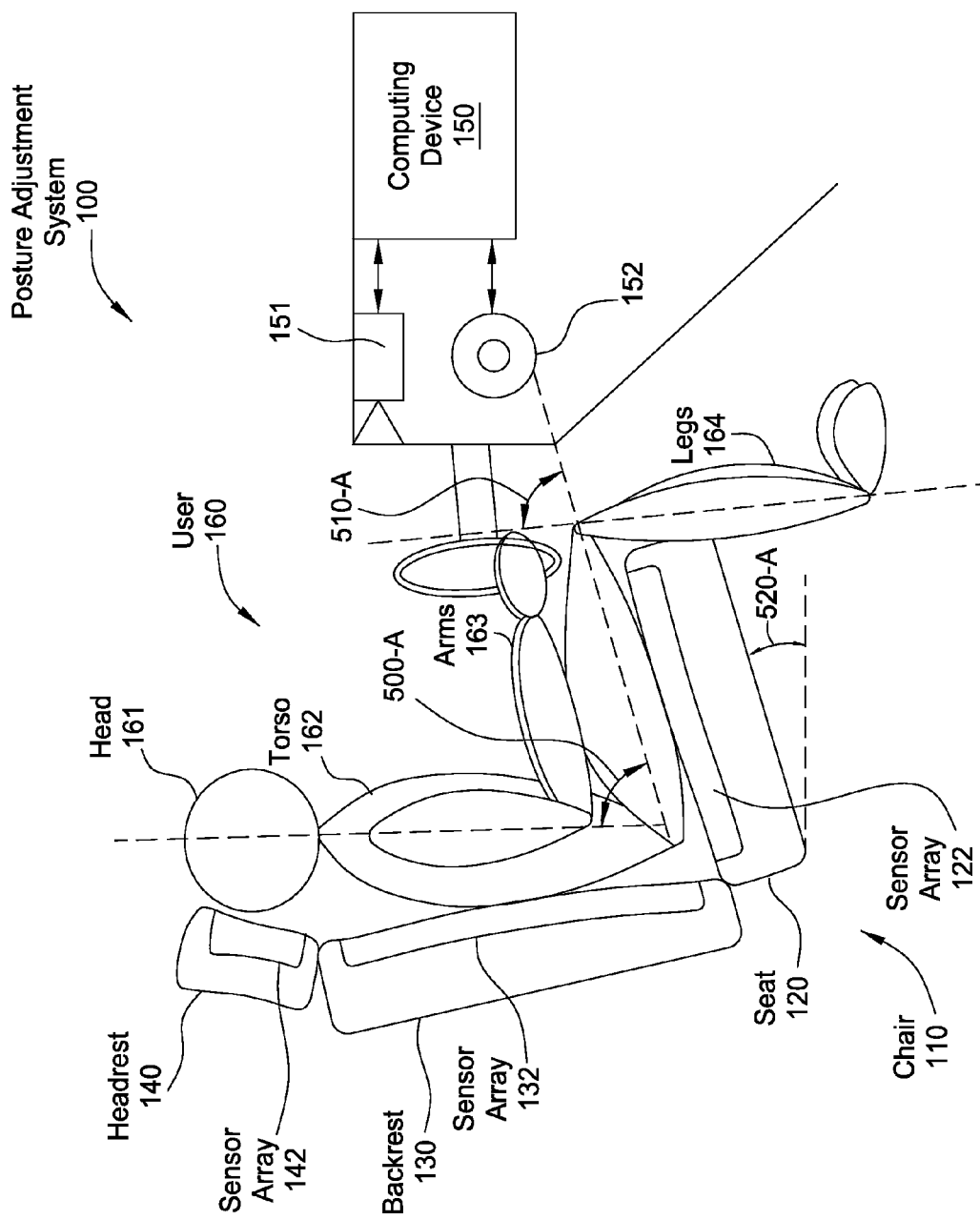
Figure 5B:
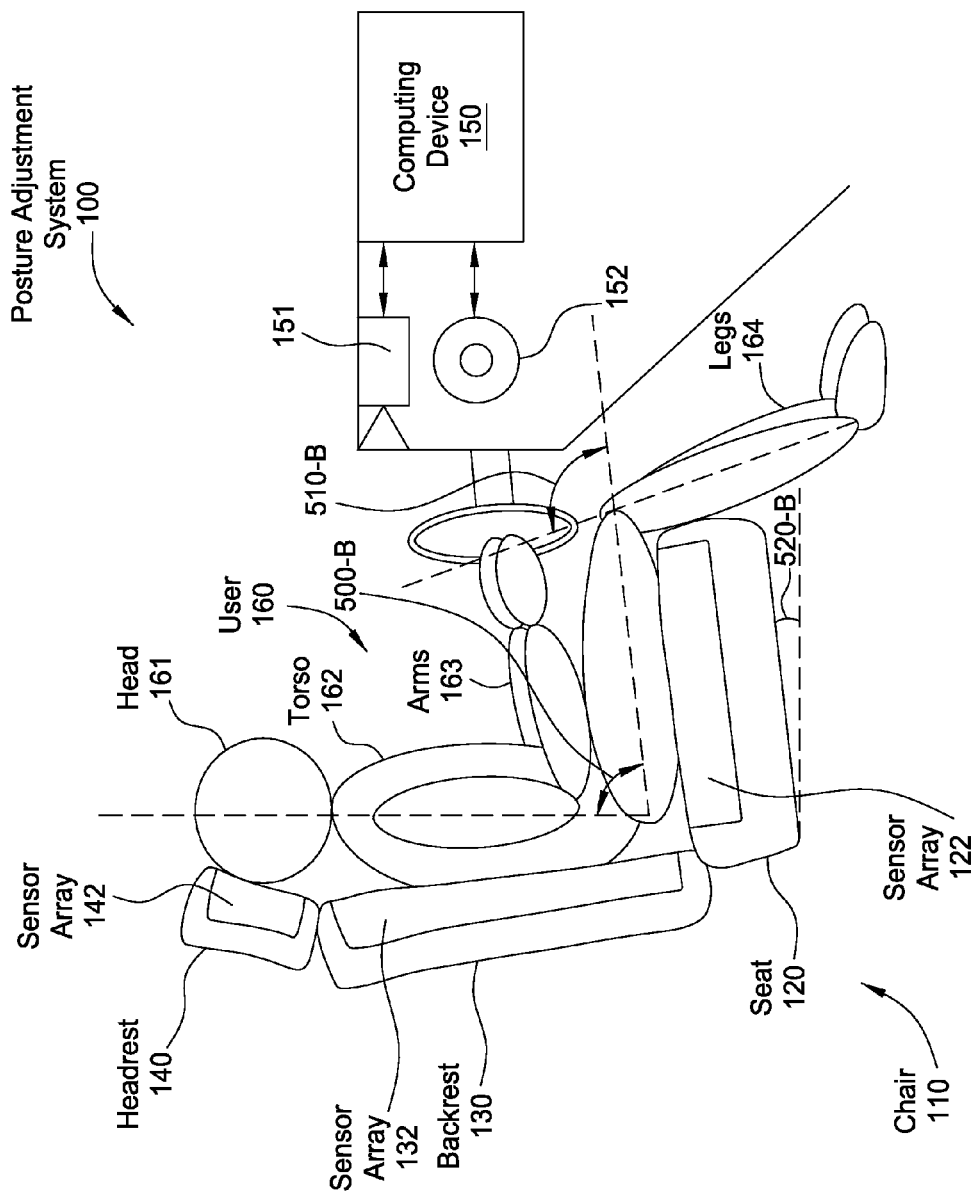

FIGS. 5A-5B illustrate an exemplary scenario where posture adjustment system 100 of FIG. 1 effects a posture correction for user 160 to modify a leg position that may be uncomfortable or health-adverse, according to various embodiments. As shown in FIG. 5A, seat 110 is positioned with an angle 520-A that substantially elevates legs 164 of user 160, thereby causing user 160 to assume a posture with excessively acute hip joint angle 500-A and similarly acute knee joint angle 510-A. Hip joint angle 500-A and knee joint angle 510-A may result in discomfort for user 160, and could potentially cause user 160 to experience leg and/or body pain over time.

Computing device 150 is configured to generate a posture model that represents the current posture of user 160 based on sensor data gathered by sensor arrays 122, 132, and 142 and/or optical sensor 151. The posture model in this example could include hip joint angle 500-A and knee joint angle 510-A, without limitation. Computing device 150 is configured to identify posture corrections that include an increase of hip joint angle 500-A and an increase of knee joint angle 510-A. Computing device then determines specific adjustments to chair 110 that may cause user 160 to assume a new posture that incorporates the aforementioned posture corrections. Computing device 150 could, for example, identify relationships between hip joint angle 500-A, knee joint angle 510-A and angle 520-A of seat 120 based on chair-posture mapping 250 shown in FIG. 2, without limitation. In various embodiments, computing device 150 may determine adjustments to chair 110 that affect any number of different posture corrections simultaneously. In the present example, computing device 150 adjusts angle 520-A of seat 110 to simultaneously correct hip joint angle 500-A and knee joint angle 510-A, as described in greater detail below in conjunction with FIG. 4B.

As shown in FIG. 5B, computing device 150 has declined seat 120 slightly by decreasing angle 520-A to angle 520-B. In response, hip joint angle 500-A has increased to hip joint angle 500-B, and knee joint angle 510-A has increased to knee joint angle 510-B. With this new posture, user 160 may avoid potential leg and/or body pain.

Figure 6B:
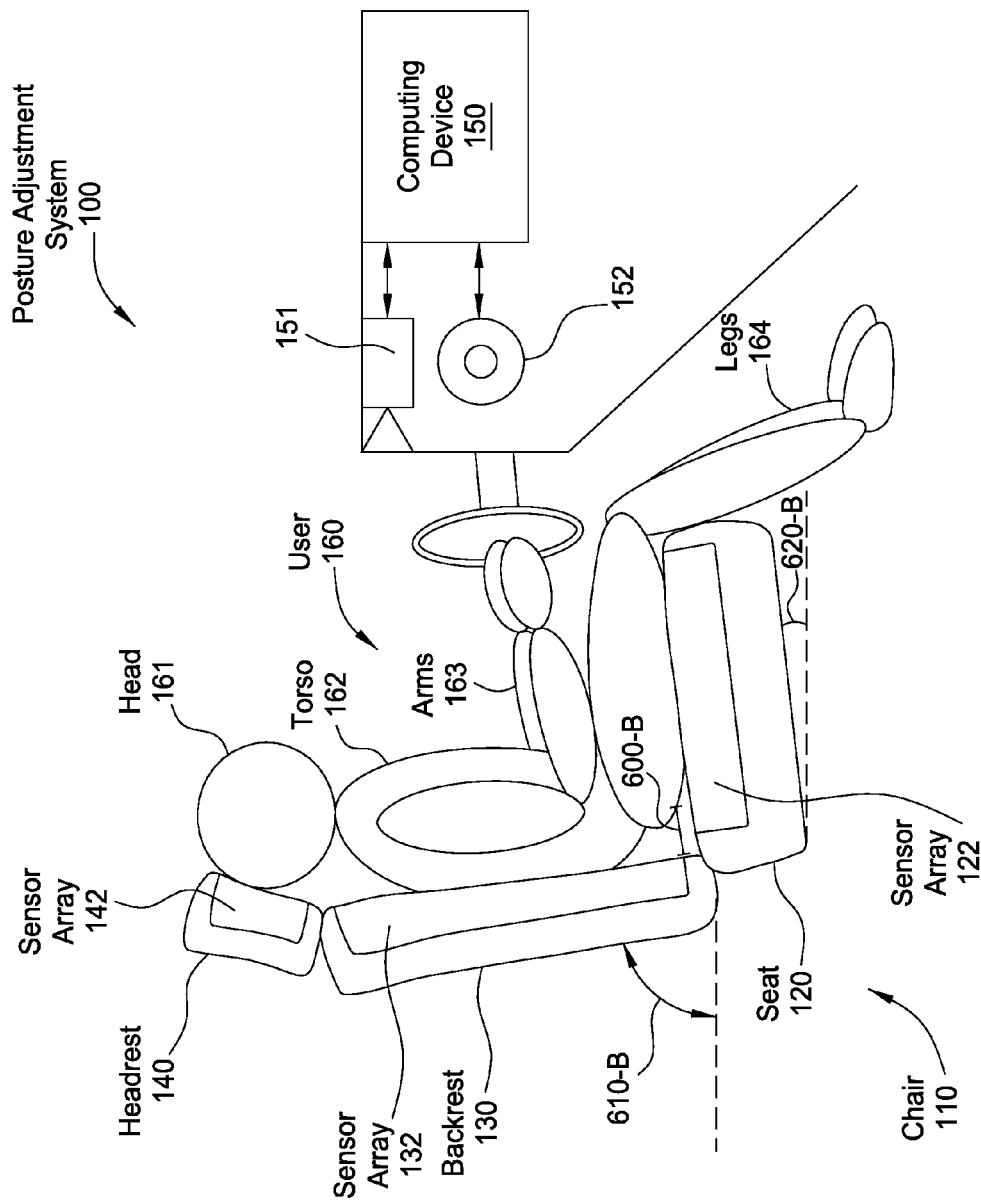

FIGS. 6A-6B illustrate an exemplary scenario where posture adjustment system 100 of FIG. 1 effects a posture correction for user 160 to mitigate a slouched posture, according to various embodiments. As shown in FIG. 6A, user 160 sits at a distance 600-A from backrest 130. Backrest 130 is positioned with an angle 610-A, while seat 110 is positioned with an angle 620-A.

Computing device 150 is configured to generate a posture model in the aforementioned fashion that reflects the current slouched posture of user 160, including distance 600-A (in the present example, without limitation). Computing device 150 identifies a posture correction that decreases the degree to which user 160 is slouched. In particular, the posture correction would indicate a decrease to distance 600-A, resulting in a more upright posture. Computing device 150 determines specific adjustments to chair 110 that may cause user 160 to assume a more upright posture that is less slouched than that shown in FIG. 6A. Computing device 150 could, for example, and without limitation, identify a relationship between distance 600-A and angles 610-A and 620-A associated with backrest 130 and seat 110, respectively, based on posture mapping 250 described above in conjunction with FIG. 2. Computing device 150 then applies the determined adjustments to chair 110 to effect the posture corrections, as described in greater detail below in conjunction with FIG. 6B.

As shown in FIG. 6B, computing device 150 has decreased angle 610-A to angle 610-B, thereby reclining backrest 630 slightly. In addition, computing device 150 has increased angle 620-A to angle 620-B, thereby elevating seat 120 slightly. In response, user 160 has assumed a new posture with a shorter distance 600-B to backrest 130. By adjusting chair 110 according to the example discussed in conjunction with FIG. 6A-6B, posture adjustment system 100 identifies complex adjustments to chair 110 that effect specific posture corrections.

Referring now more generally to FIGS. 3A-6B, posture adjustment system 100 may identify a wide variety of different posture corrections and then operate to effect those posture corrections. Posture adjustment system 100 may provide notifications to user 160 of specific posture corrections, as discussed in conjunction with FIGS. 3A-3B. Posture adjustment system 100 may also autonomously apply adjustments to chair 110 to cause user 160 to assume a new posture that reflects those posture corrections, as described above in conjunction with FIGS. 4A-6B. Posture adjustment system 100 may specifically identify individual chair sections that can be adjusted to effect posture corrections for specific body parts of user 160, as described in conjunction with FIGS. 4A-4B. Posture adjustment system 100 may also identify compound chair adjustments, involving multiple chair sections, that effect posture corrections to one or more body parts of user 160, as described above in conjunction with FIGS. 5A-6B. As a general matter, posture correction system 100 may determine and effect posture changes having any complexity, ranging from repositioning individual body parts to repositioning user 160 as a whole. A generic technique for effecting posture corrections for user 160 is described in stepwise fashion below in conjunction with FIG. 7.

Figure 7:
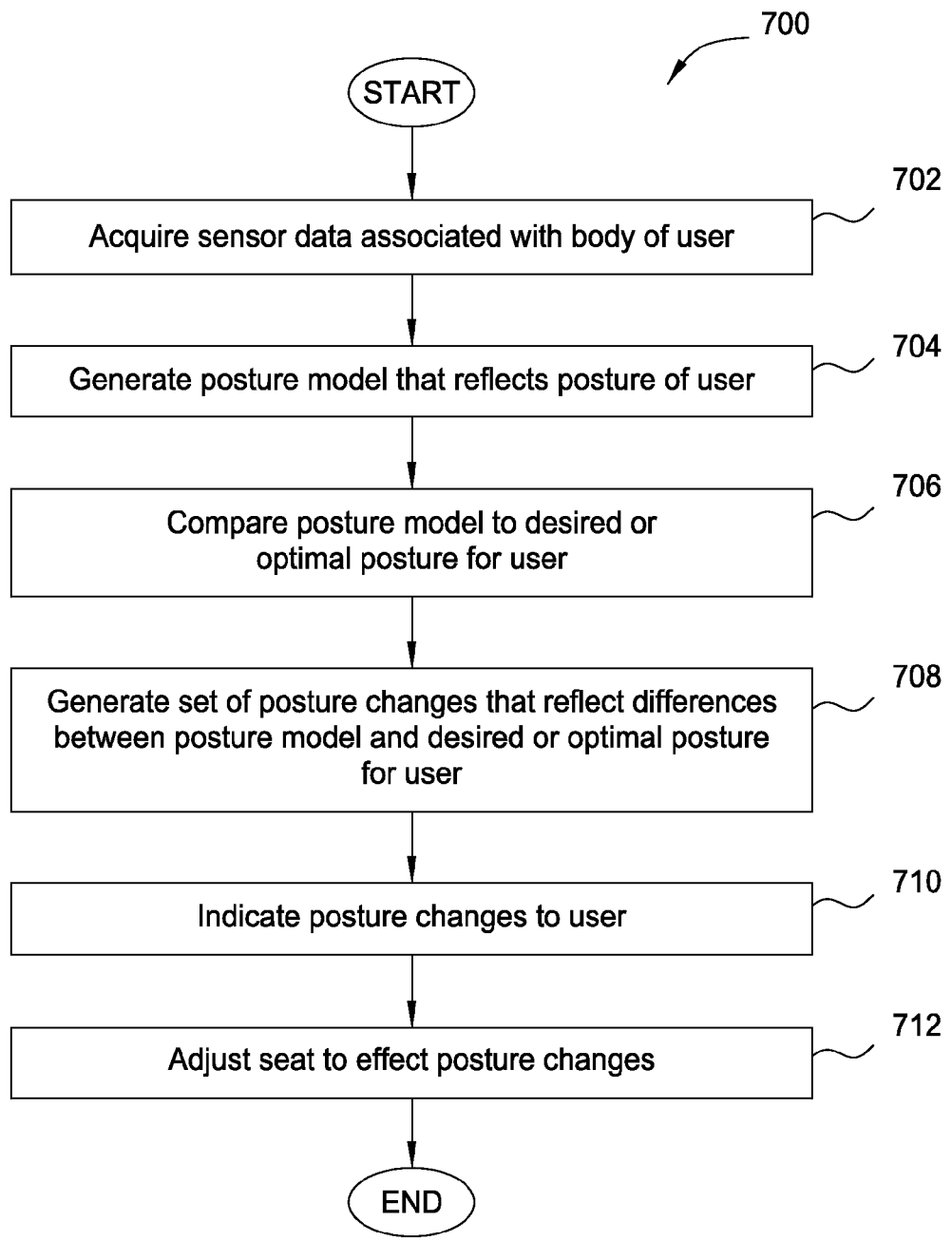
FIG. 7 is a flow diagram of method steps for modifying the posture of a seated person, according to various embodiments.

FIG. 7 is a flow diagram of method steps for adjusting the posture of a seated person, according to various embodiments of the present invention. Although the method steps are described in conjunction with the systems of FIGS. 1-6B, persons skilled in the art will understand that any system configured to perform the method steps, in any order, is within the scope of the present invention.

As shown, a method 700 begins at step 702, wherein computing device 150 within posture correction system 100 acquires sensor data associated with the body of user 160. Sensor arrays 122, 132, and 142, optical sensor 151, or any other sensor in the vicinity of user 160 may gather the sensor data. Any of the aforementioned sensors could be a capacitive touch sensor, a heat sensor, a strain gauge, a pressure sensor, a laser-based instrument, a depth measurement device, an electrical field detector, or any other technically feasible measurement device, without limitation.

At step 704, computing device 150 generates a posture model that reflects the current posture of user 160. Computing device 150 may process the sensor data acquired at step 702 locally or remotely, and may also rely on auxiliary devices (such as a smartphone or tablet computer, etc., without limitation) to perform any such processing. Any manner of computer vision, machine learning, image processing, and so forth may be implemented in conjunction with step 704 in order to generate a generic model that represents the current posture of user 160, without limitation. That model could be, for example, and without limitation, a mathematical description of body parts associated with user 160 and corresponding descriptions of linkages between those body parts.

At step 706, computing device 150 compares the posture model generated at step 704 to a desired or optimal posture for the user. The desired or optimal posture could reflect, without limitation, at least one of an ergonomic model, a set of user preferences, and a set of posture recommendation. The ergonomic model generally reflects a posture that maximizes comfort or minimizes the risk of chronic health problems. The set of user preferences may be programmed by user 160 or approximated by computing device 150 to reflect specific habits or trends associated with user 160. The posture recommendations may be received by computing device 150 over a network connection from a health professional. The health professional could be a medical doctor, a chiropractor, a yoga instructor, and so forth, without limitation. The posture recommendations generally reflect suggested postures for user 160 that may benefit the well being of user 160. The desired or optimal posture to which the posture model is compared may also reflect a combination of two or more of the ergonomic model, the set of user preferences, and the set of posture recommendations.

At step 708, computing device 150 generates a set of posture changes that reflect differences between the posture model generated at step 702 and the desired or optimal posture. The set of posture changes generally represents corrections or modifications to the current posture of user 160 that would bring that posture into closer alignment with the desired or optimal posture, including one or more of the ergonomic model, the set of user preferences, and the set of posture recommendations.

At step 710, computing device 150 indicates the posture changes generated at step 708 to user 160. Computing device 150 may audibly indicate those posture changes to user 160, e.g., via speaker 151, visually convey those changes, or otherwise notify user 160 of the posture changes. With this approach, user 160 is provided with the opportunity to perform self-correction, which, over time, may improve the self-awareness of user 160. In performing step 710, computing device 150 may also notify user 160 of adjustments to chair 110 to be effected at a later time, potentially avoiding situations where user 160 is startled or caught off-guard by those adjustments.

At step 712, computing device 150 adjusts a seat associated with posture adjustment system 100 to effect the posture changes generated at step 708. In one embodiment, computing device 150 relies on a chair-posture mapping that indicates specific relationships between the position of specific sections of the chair and the position of specific body parts of user 160. Based on this data, computing device 150 may determine specific adjustments to those chair sections that would result in the posture changes generated at step 708. The method 700 then ends.

In performing the method 700, computing device 150 may optionally perform either step 710 or step 712, or perform both of those steps. Computing device 150 may also selectively perform just one of steps 710 and 712 depending on various environmental factors, the specific postures changes to be made, or user preferences, among other things. User 160 could, for example, configure computing device 150 to only perform step 710 when the posture changes involve the head of user 160, and to only perform step 712 when the posture changes involve other body parts of user 160. Posture adjustment system 100 may also be configured to effect modifications to the posture of user 160 relative to trends or patterns, as described in stepwise fashion below in conjunction with FIG. 8.

Figure 8:
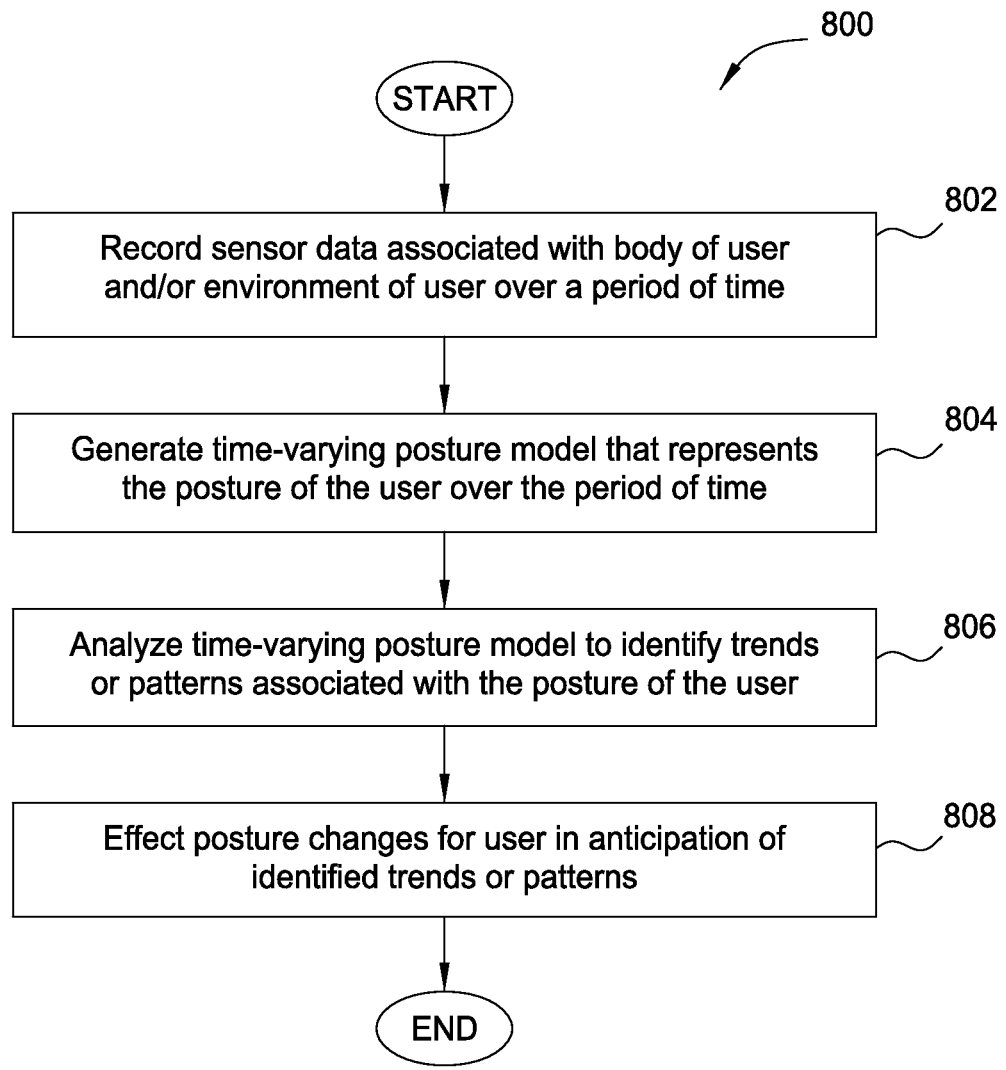
FIG. 8 is a flow diagram of method steps for modifying the posture of a seated person relative to a trend associated with the person, according to various embodiments.

FIG. 8 is a flow diagram of method steps for modifying the posture of a seated person relative to a trend associated with the person, according to various embodiments. Although the method steps are described in conjunction with the systems of FIGS. 1-6B, persons skilled in the art will understand that any system configured to perform the method steps, in any order, is within the scope of the present invention.

As shown, a method 800 begins at step 802, where computing device 150 within posture adjustment system 100 records sensor data associated the body of user 160 and/or the environment of user 160 over a period of time. The sensor data could be gathered by sensor arrays 122, 132, or 142, optical sensor 151, or acquired from a suite of sensors configured to measure properties of the environment where user 160 resides. That environment could include a car within which posture adjustment system 100 is incorporated, an office where posture adjustment system 100 is in use, and so forth, without limitation.

At step 804, computing device 150 generates a time-varying posture model that represents the posture of user 160 over a period of time. The time-varying posture model generally reflects posture trends and/or patterns that may be determined based on the sensor data recorded at step 802. In addition, the time-varying posture model may also indicate other data associated with the environment of user that may cause variations in the posture of user 160 over time. For example, in the context of an automobile, the time-varying posture model could indicate that user 160 typically assumes a slouched posture when cruise control is activated for longer than 30 minutes, without limitation.

At step 806, computing device 150 analyzes the time-varying posture model to identify trends or patterns associated with the posture of the user 160. Those trends or patterns could reflect correlations between the posture of user 160 and various times, events, environmental cues, configurations of an automobile that user 160 drives, other actions performed by user 160, and so forth, without limitation.

At step 808, computing device 150 effects one or more posture changes for user 160 in anticipation of an identified trend or pattern. Again, the trend could simply reflect patterns in the posture of use 160 over time, or responses of that posture to environmental factors. In either case, at step 808 computing device 150 computes one or more posture changes in anticipation of the identified trend or pattern, and then effects those posture changes in advance of that trend. Returning to the example cited in conjunction with step 804, computing device 150 could, at step 808, determine that cruise control has been activated for longer than 30 minutes and then automatically effect adjustments to chair 110 that preclude slouching, thereby anticipating that behavior of user 160, without limitation. The method 800 then ends.

Those skilled in the art will recognize that the techniques described above in conjunction with FIGS. 1-7 may be implemented by a wide variety of different types of systems configured to process and manage data, including, without limitation, microchips, arrays of processing units, field-programmable gate arrays (FPGAs), system-on-chips (SOCs), remote server machines and other cloud-based computing devices. The aforementioned techniques may also be performed by portable computing devices carried or worn by user 160, such as cell phones, tablet computers, smart watch devices and other wearables, and so forth, without limitation. One example of a computing device configured to manage the functionality of posture adjustment system 100 is described below in conjunction with FIG. 9.

Figure 9:
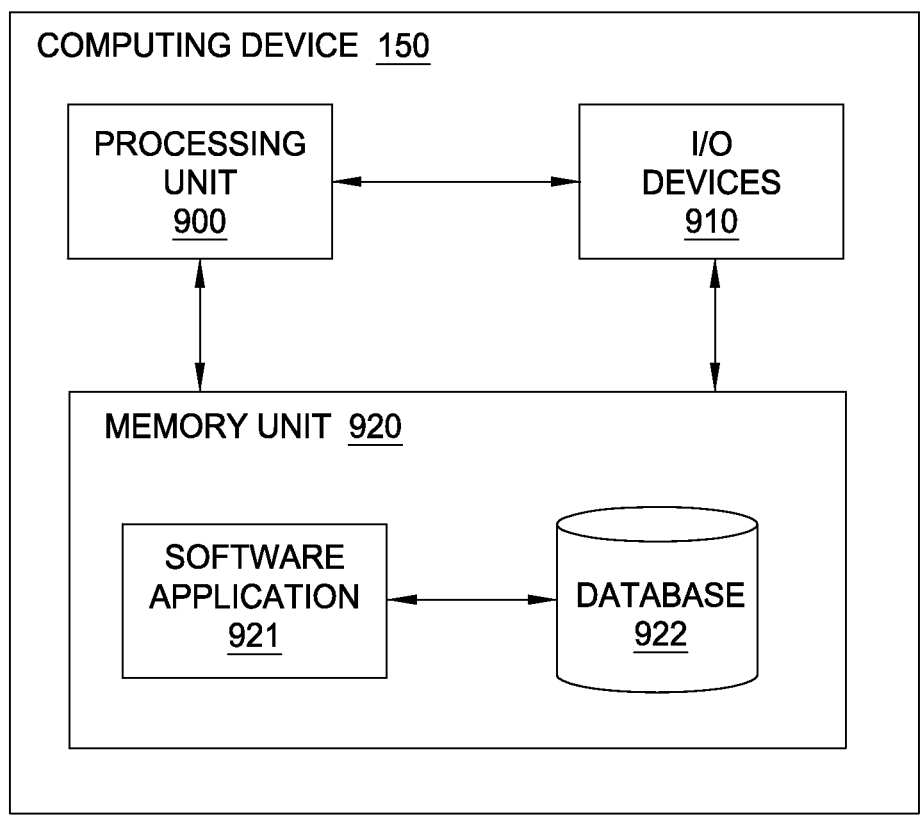
FIG. 9 is a block diagram of a computing device configured to manage the operation of the posture adjustment system of FIG. 1, according to various embodiments.

FIG. 9 is a block diagram of computing device 150 configured to manage the operation of posture adjustment system 100 of FIG. 1, according to various embodiments of the present invention. As shown, computing device 150 includes a processing unit 900, input/output (I/O) devices 910, and a memory unit 920 coupled to one another. Memory unit 920 includes a software application 921 and a database 922.

Processing unit 900 may be any technically feasible hardware unit configured to process data, including, without limitation, a central processing unit (CPU), a graphics processing unit (GPU), a parallel processing unit (PPU), an application-specific integrated circuit (ASIC), and so forth, without limitation. I/O devices 910 include devices configured to receive input, such as a sensor array, a control panel, and so forth, devices configured to provide output, such as a speaker, a video display, haptic and tactile actuators, a motor, servo and other effectors, and so forth, as well a devices configured to both receive input and generate output, such as a touchscreen, a network interface, etc., without limitation. I/O devices 910 may also include wireless transceivers capable of establishing local area network (LAN) connections and/or wide area network (WAN) connections, thereby providing connectivity to other devices as well as to the Internet. Memory unit 920 may be any type of readable and/or writable storage media, including a random access memory (RAM), a hard disk, a combination of memory modules, and so forth, without limitation.

Software application 921 includes program code that is executable by processing unit 900 to perform the functionality of posture adjustment system 100 described herein. Software application 921 may read data from and write data to a database 922. The data stored within database 922 may include posture models, ergonomic models, user preferences, posture recommendations, posture-chair mapping data, or profile data for a given user that reflects any of the aforementioned data. Software application 921 may execute a wide range of processing algorithms to process sensor data acquired by computing device 150, including, but not limited to, computer vision algorithms, object recognition programs, and multidimensional modeling tools, among others. Software application 921 may also include any type of operating system, motor control signal generators, a text-to-voice application, a graphical user interface (GUI), and any other type of software needed to implement any of the functionality described herein. Persons skilled in the art will recognize that the techniques described thus far may be implemented via program instructions within software application 921, in hardware by processing unit 900, executed remotely via cloud-based services, or performed via any combination of the processing methodologies listed thus far.

In sum, a posture adjustment system includes a set of sensors coupled to a chair on which a person may sit. The posture adjustment system gathers data from the set of sensors and generates a posture model that reflects a posture associated with the seated person. The posture adjustment system then determines corrections to the posture of the person that could, potentially, improve their posture. The posture adjustment system then indicates those corrections to the person, or, alternatively, applies a set of adjustments to the chair to cause the person to assume a new posture that reflects the posture corrections.

One advantage of the present invention is that the health and well being of a user of the posture adjustment system may be improved. When a user habitually sits with a posture that may be detrimental to their health, the posture adjustment system is capable of identifying the detrimental posture and taking corrective action. In addition, the posture adjustment system can be configured to reflect input received from medical professionals, thereby enhancing the degree to which the posture adjustment system can improve the posture of the user. When integrated into an automobile, the posture adjustment system may increase driver safety by alleviating posture-related distractions, including discomfort and pain. As such, the posture adjustment system described herein represents a significant advancement towards mitigating the ill effects of poor posture.

One embodiment of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as compact disc read only memory (CD-ROM) disks readable by a CD-ROM drive, flash memory, read only memory (ROM) chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments. Persons of ordinary skill in the art, however, will understand that various modifications and changes may be made thereto without departing from the broader spirit and scope of the invention as set forth in the appended claims. The foregoing description and drawings are, accordingly, to be regarded in an illustrative rather than a restrictive sense.

Therefore, the scope of embodiments of the present invention is set forth in the claims that follow.

What is claimed is:

1. A non-transitory computer-readable medium storing program instructions that, when executed by a processing unit, cause the processing unit to effect modifications to the posture of a seated person, by performing the steps of:
    acquiring sensor data that reflects a current posture associated with the seated person;
    determining at least one modification to make to the current posture to change the current posture to a modified posture;
    generating one or more chair adjustments to be applied to a chair in which the seated person is sitting to change the current posture to the modified posture based on the at least one modification and a chair-posture mapping indicating changes in position or orientation of each section of the chair and corresponding changes in posture of a person sitting in the chair; and
    applying the one or more chair adjustments to the chair in which the seated person is sitting to automatically change the current posture of the seated person to the modified posture.

2. The non-transitory computer-readable medium of claim 1, further comprising the step of generating a first posture model that includes a mathematical description of the current posture.

3. The non-transitory computer-readable medium of claim 2, wherein the step of determining the at least one modification comprises:
    comparing the first posture model to a second posture model;
    identifying one or more differences between the first posture model and the second posture model; and
    determining a modification to the first posture model that causes the first posture model to more closely approximate the second posture model.

4. The non-transitory computer-readable medium of claim 2, wherein the step of determining the at least one modification comprises:
    comparing the first posture model to a set of preferences associated with the seated person that reflects a preferred posture of the seated person; and
    determining a modification to the first posture model that causes the first posture model to more closely approximate the preferred posture.

5. The non-transitory computer-readable medium of claim 2, wherein the step of determining the at least one modification comprises:
    comparing the first posture model to a set of posture recommendations received from a medical professional that reflects a recommended posture for the seated person; and
    determining a modification to the first posture model that causes the first posture model to more closely approximate the recommended posture.

6. The non-transitory computer-readable medium of claim 1, wherein generating the one or more chair adjustments comprises:
    determining that a first position of the section of the chair corresponds to the current posture;
    determining that a second position of the section of the chair corresponds to the modified posture;
    comparing the first position to the second position to determine a position difference; and
    determining an adjustment to the section of the chair based on the position difference and the chair-posture mapping.

7. A system for adjusting the posture of a person, the system comprising:
    a sensor array configured to generate sensor data that indicates a first location associated with a portion of the person;
    a first section of a chair in physical contact with the portion of the person and having a first position; and
    a computing device configured to:
        generate one or more chair adjustments to be applied to the first section of the chair to relocate the portion of the person from the first location to a second location based on a chair-posture mapping indicating changes in position or orientation of each section of the chair and corresponding change in posture of a person sitting in the chair, and
        apply the one or more chair adjustments to the first section of the chair to cause the first section of the chair to reposition automatically from the first position to a second position to relocate the portion of the person from the first location to a second location.

8. The system of claim 7, further comprising a motor coupled to the first section of the chair, and wherein the computing device causes the first section of the chair to be repositioned by:
    identifying the second location to which the portion of the person should be relocated;
    determining that the first section of the chair can be repositioned from the first position to the second position to cause the portion of the person to relocate from the first location to the second location; and
    issuing a motor control signal to the motor that causes the motor to move the first section of the chair from the first position to the second position.

9. The system of claim 8, wherein identifying the second position comprises analyzing data that reflects a set of target positions for different portions of the person.

10. The system of claim 7, wherein the chair resides within an automobile.

11. The system of claim 7, wherein the chair comprises an office chair residing in an office environment.

12. The system of claim 7, wherein the sensor array is coupled to the first section of the chair and is configured to measure at least one of pressure and heat associated with the person.

13. A computer-implemented method for modifying the posture of a user, the method comprising:
generating a first posture model that reflects a current posture associated with the user;
comparing the first posture model to a second posture model to identify a set of posture modifications;
generating one or more chair adjustments to be applied to a chair in which the seated person is sitting to change the current posture to a modified posture that reflects the second posture model based on the set of posture modifications and a chair-posture mapping indicating changes in position or orientation of each section of the chair and corresponding changes in posture of a person sitting in the chair; and
applying the one or more chair adjustments to at least a first section of a chair in which the user is sitting to automatically change the current posture of the user to the modified posture.

14. The computer-implemented method of claim 13, wherein generating the first posture model comprises acquiring sensor data that reflects a first set of locations associated with the one or more body parts of the user.

15. The computer-implemented method of claim 14, wherein the second posture model comprises a mathematical description of the modified posture, and wherein comparing the first posture model to the second posture model comprises comparing the first set of locations associated with the one or more body parts to a second set of locations associated with one or more virtual body parts associated with the second posture model.

16. The computer-implemented method of claim 13, wherein the chair includes a first section and a motor coupled to a first section, wherein the motor is configured to receive motor signals that are based on at least a portion of the set of posture modifications and to reposition the first section of the chair in response to the motor signals.

* * * * *